(12) United States Patent
Salahieh et al.

US007651514B2

(10) Patent No.: US 7,651,514 B2
(45) Date of Patent: Jan. 26, 2010

(54) NOSE RIDER IMPROVEMENT FOR FILTER EXCHANGE AND METHODS OF USE

(75) Inventors: Amr Salahieh, Saratoga, CA (US); Brian J. Lowe, Zimmerman, MN (US); Thomas E. Broome, Shakopee, MN (US); Mel R. Beulke, Bloomington, MN (US); Jackson Demond, Santa Cruz, CA (US); Richard Renati, Los Gatos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 681 days.

(21) Appl. No.: 10/734,849

(22) Filed: Dec. 11, 2003

(65) Prior Publication Data
US 2005/0131449 A1     Jun. 16, 2005

(51) Int. Cl.
*A61M 29/00* (2006.01)
(52) U.S. Cl. ...................................... 606/200
(58) Field of Classification Search .................. 606/200, 606/194; 623/1.23
See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,447,227 A | 5/1984 | Kotsanis | |
| 4,580,568 A | 4/1986 | Gianturco | |
| 4,590,938 A | 5/1986 | Segura et al. | |
| 4,619,246 A | 10/1986 | Molgaard-Nielsen et al. | |
| 4,631,052 A | 12/1986 | Kensey | |
| 4,643,184 A | 2/1987 | Mobin-Uddin | |
| 4,650,466 A | 3/1987 | Luther | |

(Continued)

FOREIGN PATENT DOCUMENTS

DE        28 21 048       7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Darwin P Erezo
(74) *Attorney, Agent, or Firm*—Crompton, Seager & Tufte LLC

(57) ABSTRACT

Systems and methods for transporting intravascular devices through a body lumen are disclosed. A filter system in accordance with an exemplary embodiment of the present invention may include a guide tip having a guidewire lumen adapted to receive a guidewire, an elongated wire operatively coupled to an embolic protection filter, and a filter delivery device including an elongated tubular member extending distally to a distal sheath, the elongated tubular member may include a first lumen adapted to receive the elongated wire, and a second lumen adapted to receive the guidewire.

38 Claims, 16 Drawing Sheets

U.S. PATENT DOCUMENTS

| | | |
|---|---|---|
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford, III et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenther et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazerus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson et al. |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vorwerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren et al. |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |

| | | |
|---|---|---|
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 * | 1/2001 | Khosravi et al. ............ 606/200 |
| 6,203,561 B1 * | 3/2001 | Ramee et al. ............... 606/200 |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 * | 9/2001 | Cryer et al. ................. 606/200 |
| 6,309,399 B1 | 10/2001 | Barbut et al. |
| 6,319,268 B1 | 11/2001 | Ambrisco et al. |
| 6,336,934 B1 | 1/2002 | Gilson et al. |
| 6,344,049 B1 | 2/2002 | Levinson et al. |
| 6,361,546 B1 | 3/2002 | Khosravi |
| 6,371,969 B1 | 4/2002 | Tsugita et al. |
| 6,371,970 B1 * | 4/2002 | Khosravi et al. ............ 606/200 |
| 6,371,971 B1 | 4/2002 | Tsugita et al. |
| 6,391,044 B1 | 5/2002 | Yadav et al. |
| 6,432,122 B1 | 8/2002 | Gilson et al. |
| 6,468,291 B2 | 10/2002 | Bates |
| 6,485,501 B1 | 11/2002 | Green |
| 6,537,294 B1 * | 3/2003 | Boyle et al. ................. 606/200 |
| 6,540,722 B1 | 4/2003 | Boyle et al. |
| 6,544,279 B1 | 4/2003 | Hopkins et al. |
| 6,544,280 B1 | 4/2003 | Daniel et al. |
| 6,565,591 B2 | 5/2003 | Brady et al. |
| 6,569,184 B2 | 5/2003 | Huter |
| 6,575,996 B1 | 6/2003 | Denison et al. |
| 6,589,263 B1 | 7/2003 | Hopkins et al. |
| 6,596,011 B2 | 7/2003 | Johnson et al. |
| 6,605,102 B1 | 8/2003 | Mazzocchi et al. |
| 6,616,679 B1 | 9/2003 | Khosravi et al. |
| 6,616,680 B1 | 9/2003 | Thielen |
| 6,616,682 B2 | 9/2003 | Joergensen et al. |
| 6,620,182 B1 * | 9/2003 | Khosravi et al. ............ 606/200 |
| 6,635,070 B2 | 10/2003 | Leeflang et al. |
| 6,645,224 B2 | 11/2003 | Gilson et al. |
| 6,656,351 B2 | 12/2003 | Boyle |
| 6,660,021 B1 | 12/2003 | Palmer et al. |
| 6,695,813 B1 * | 2/2004 | Boyle et al. .................. 604/106 |
| 6,755,846 B1 * | 6/2004 | Yadav ......................... 606/200 |
| 6,997,938 B2 * | 2/2006 | Wang et al. .................. 606/200 |
| 7,144,408 B2 * | 12/2006 | Keegan et al. ............... 606/200 |
| 7,163,550 B2 * | 1/2007 | Boismier ..................... 606/200 |
| 7,235,061 B2 * | 6/2007 | Tsugita ....................... 604/104 |
| 7,241,304 B2 * | 7/2007 | Boyle et al. ................. 606/200 |
| 7,425,215 B2 * | 9/2008 | Boyle .......................... 606/200 |
| 2003/0023263 A1 * | 1/2003 | Krolik et al. ................. 606/200 |
| 2003/0078614 A1 | 4/2003 | Salahieh et al. |

FOREIGN PATENT DOCUMENTS

| | | |
|---|---|---|
| DE | 34 17 738 | 11/1985 |
| DE | 40 30 998 A1 | 10/1990 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 297 797 A2 | 4/2003 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |

| | | |
|---|---|---|
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |

OTHER PUBLICATIONS

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," The New England Journal of Medicine, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," *Laboratory Investigation*, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," *Catheterization and Cardiovascular Diagnosis*, 31:17-84 (1994).

Moussa, MD, Issaam "Stents Don't Require Systemic Anticoagulation . . . But the Technique (and Results) Must be Optimal," *Journal of Invasive Cardiol.*, 8(E):3E-7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386-392 (1998).

Theron et al., "New Triple Coaxial Catheter System for Carotid Angioplasty with Cerebral Protection," *American Journal of Neuroradiology*, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

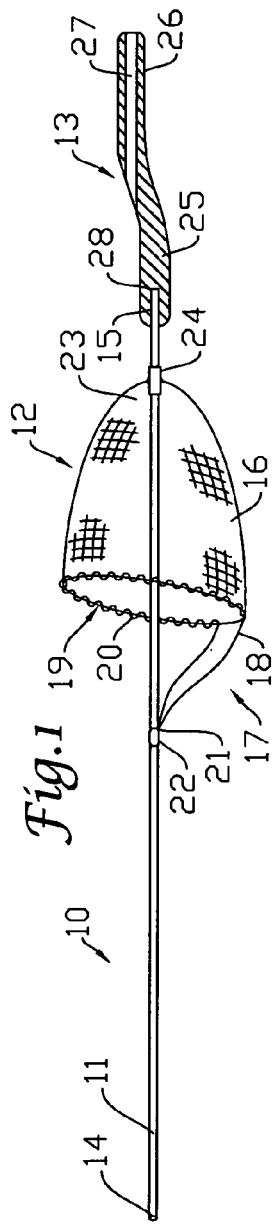
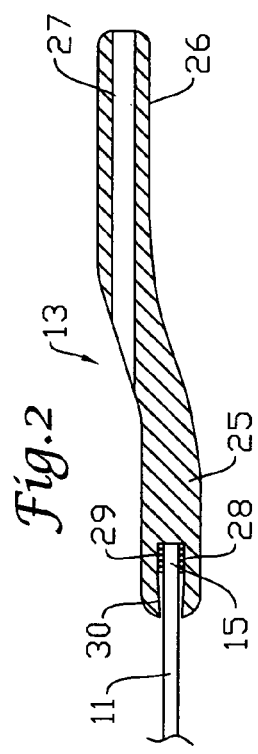
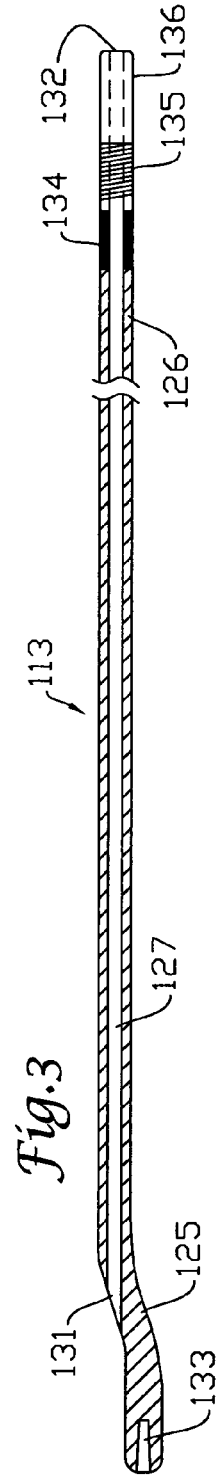
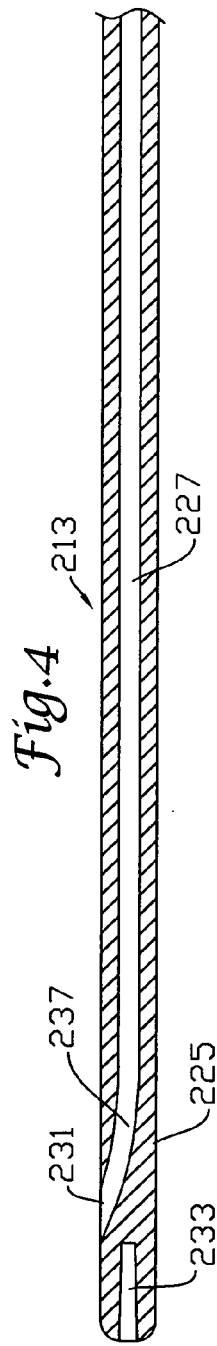

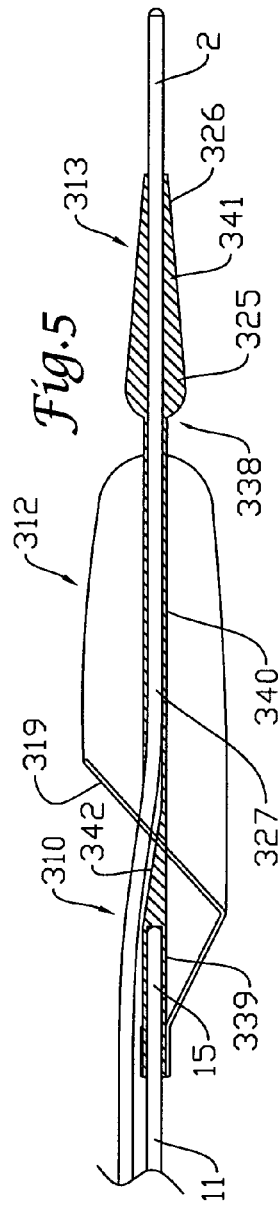
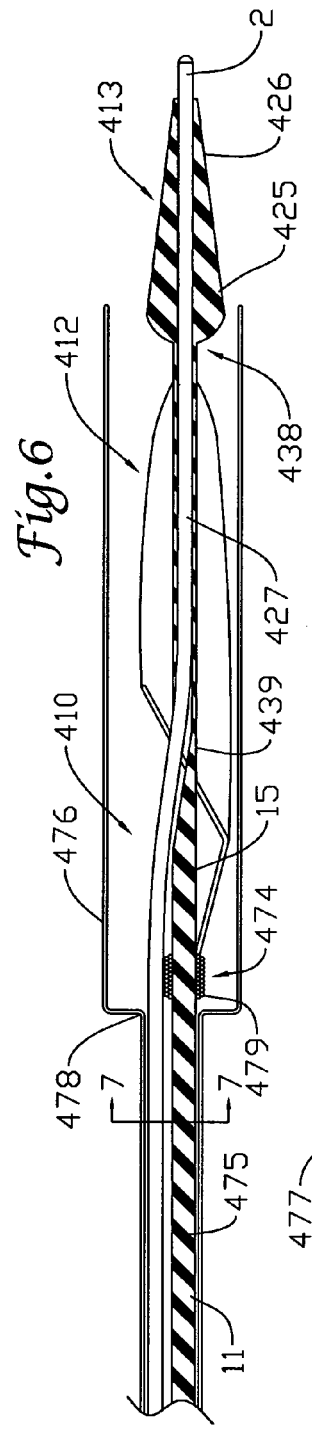
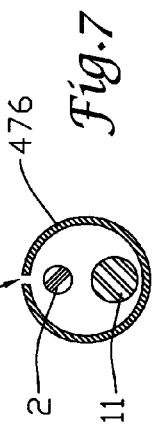
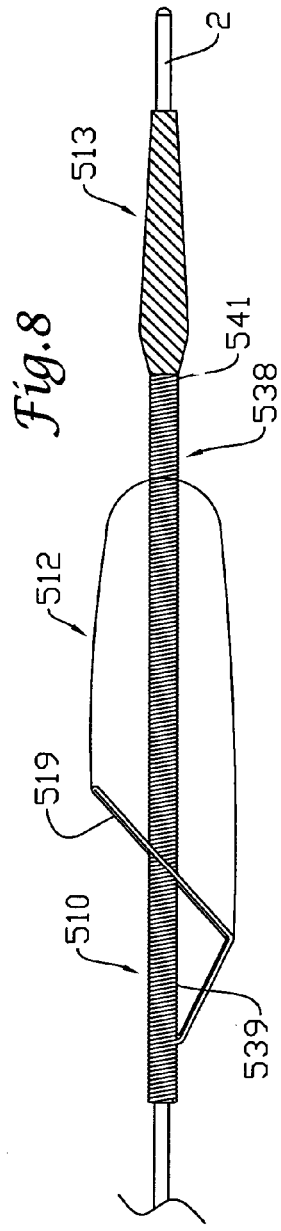

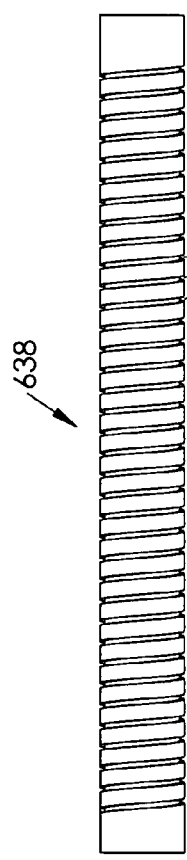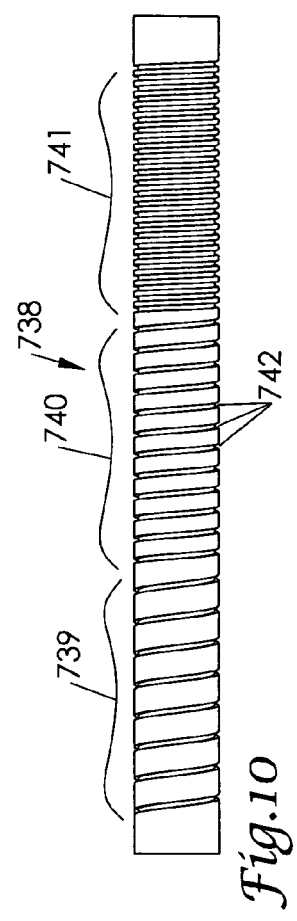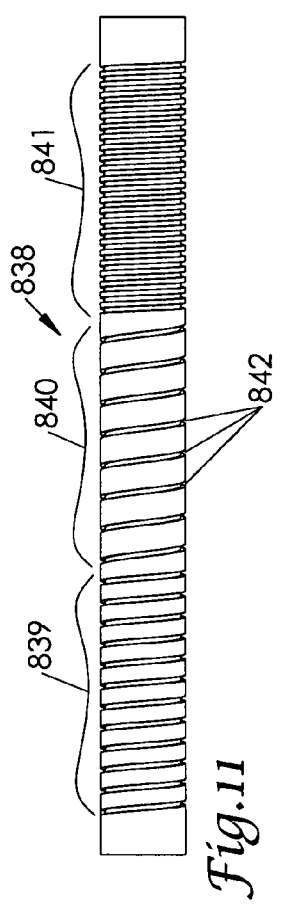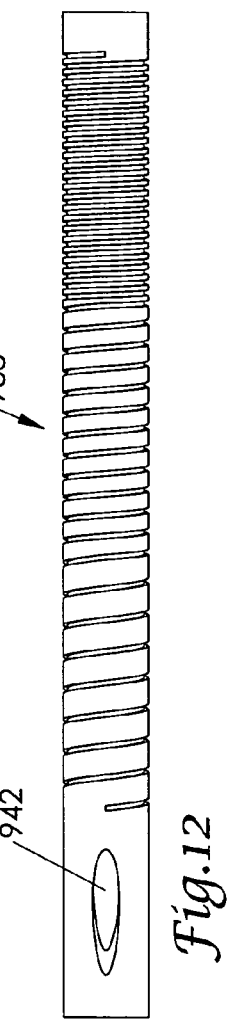

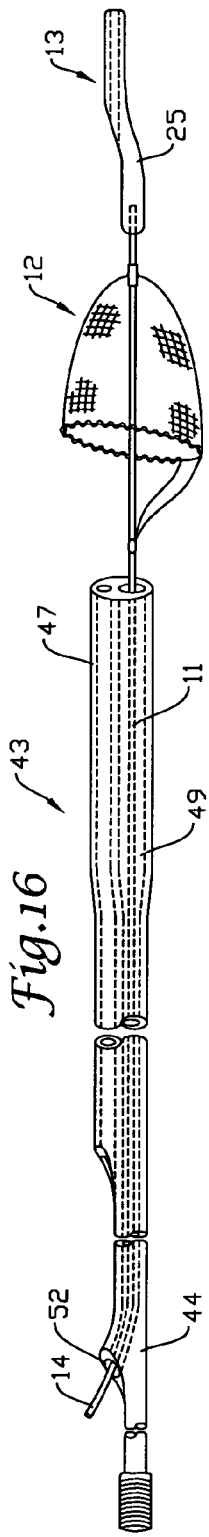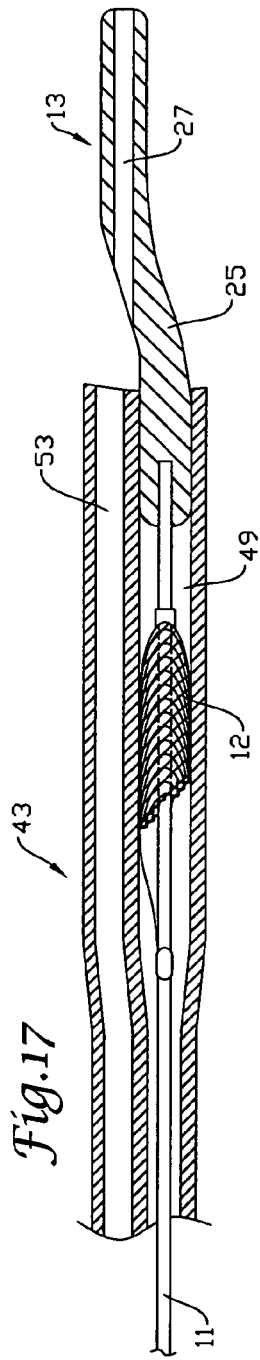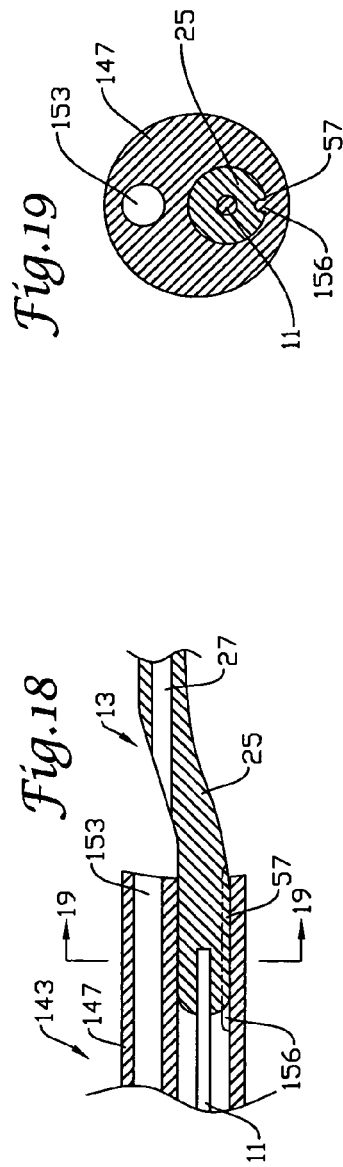

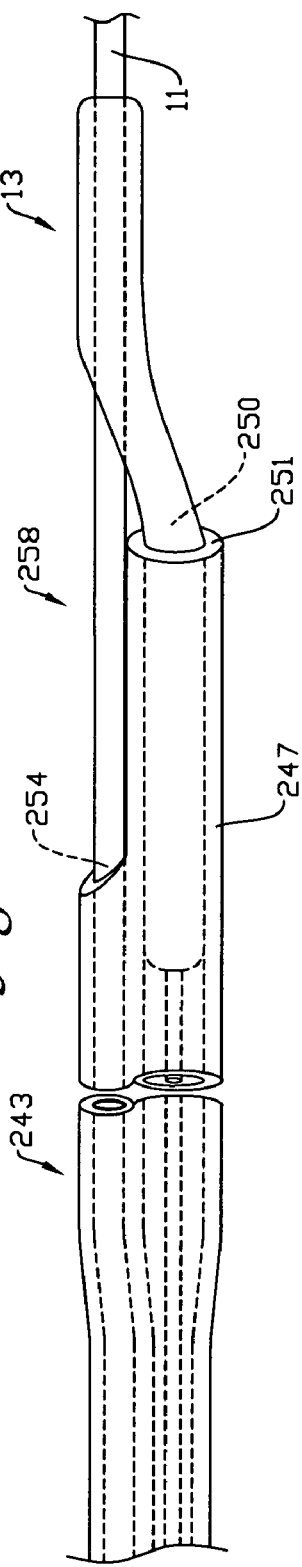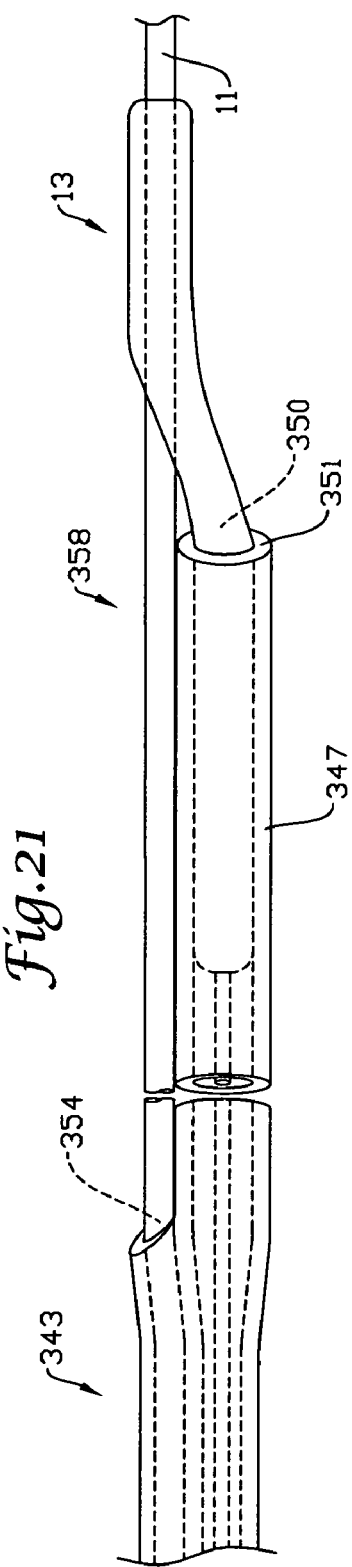

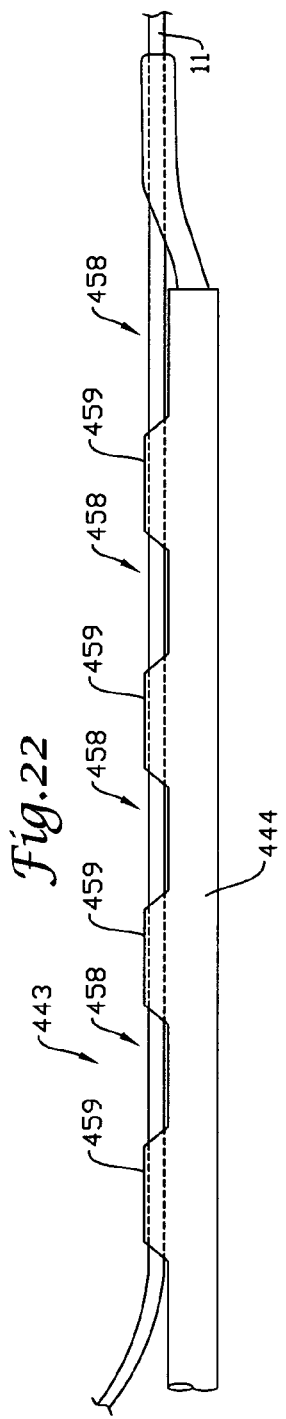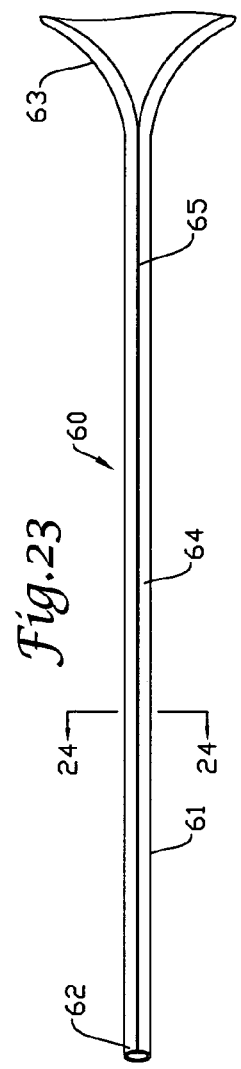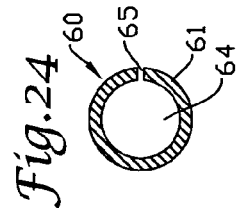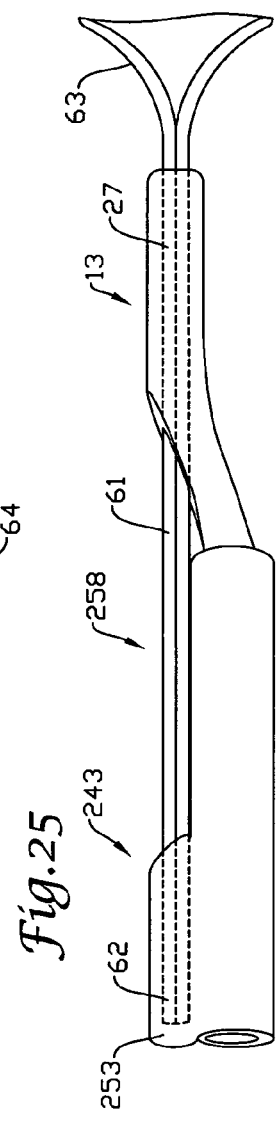

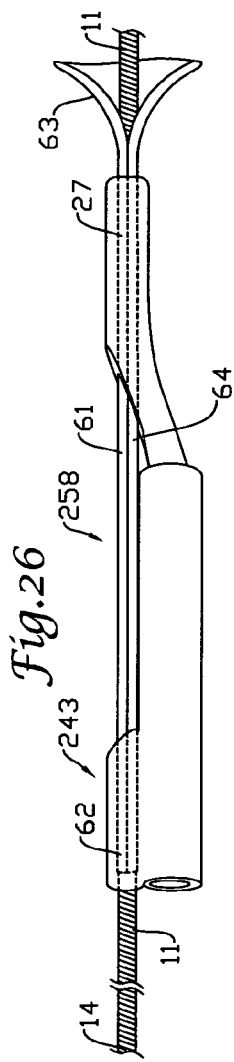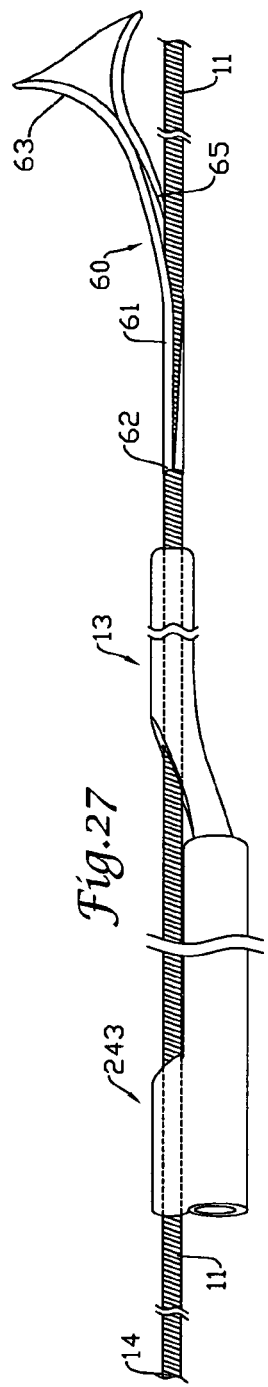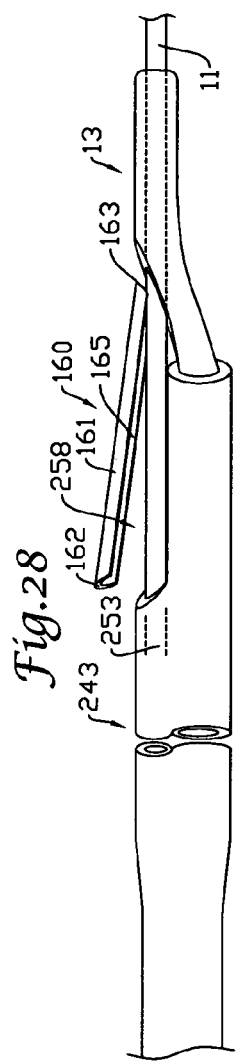

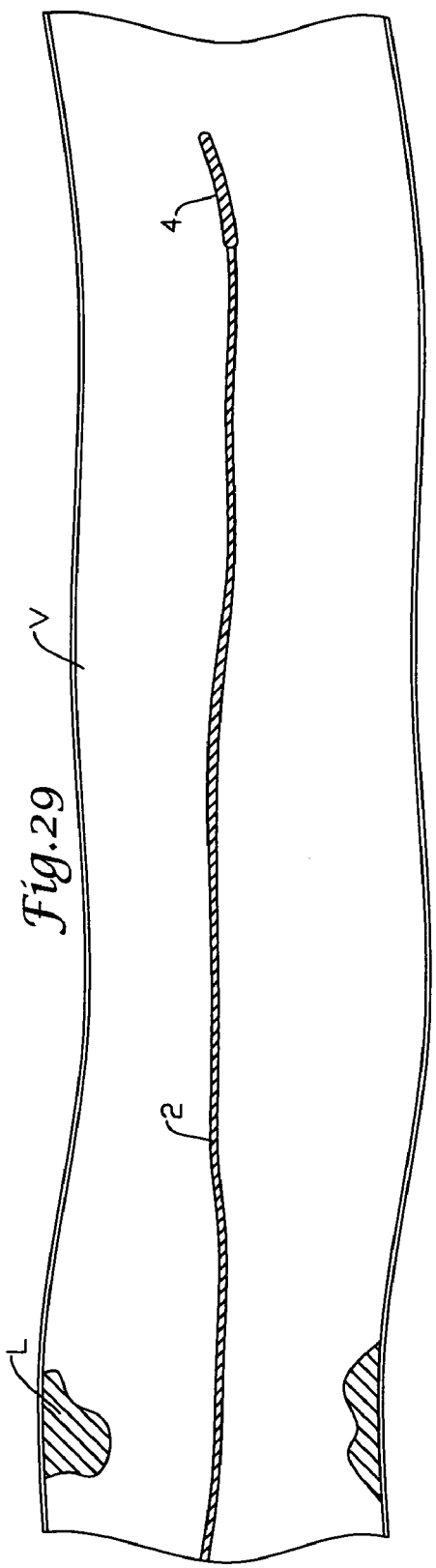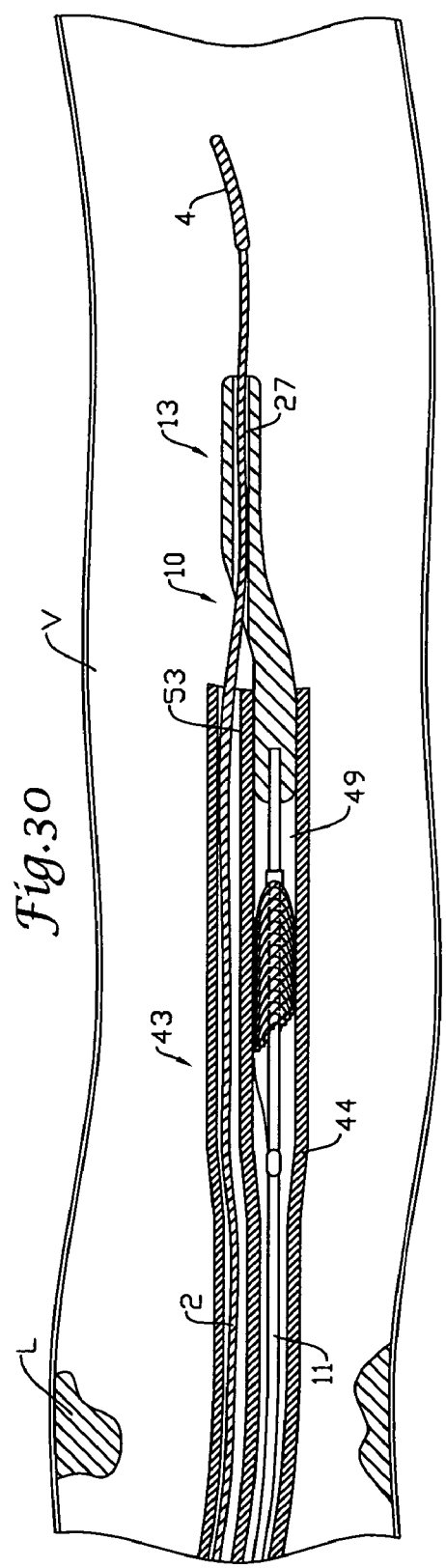

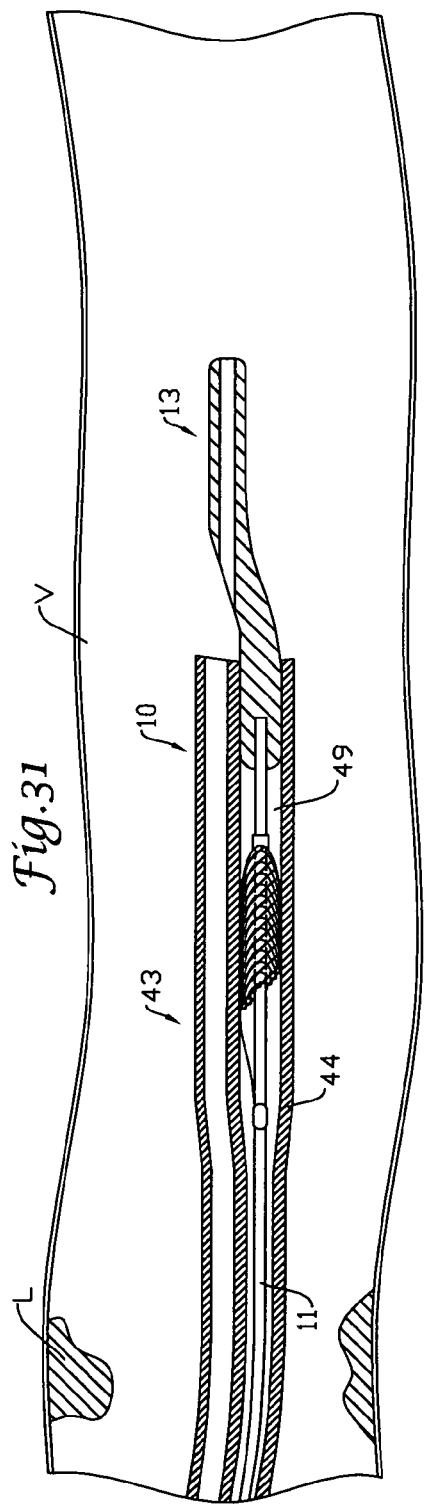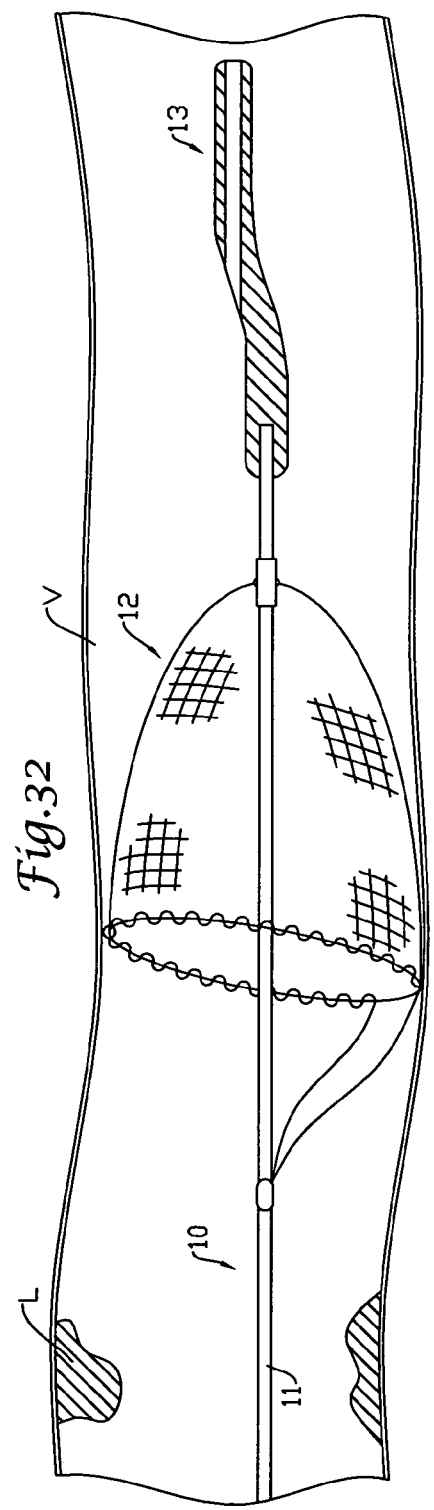

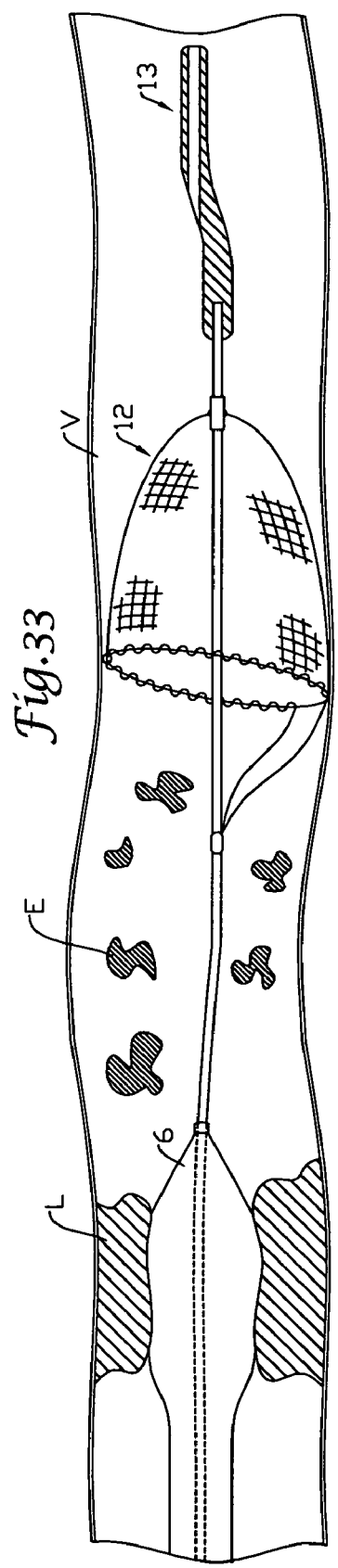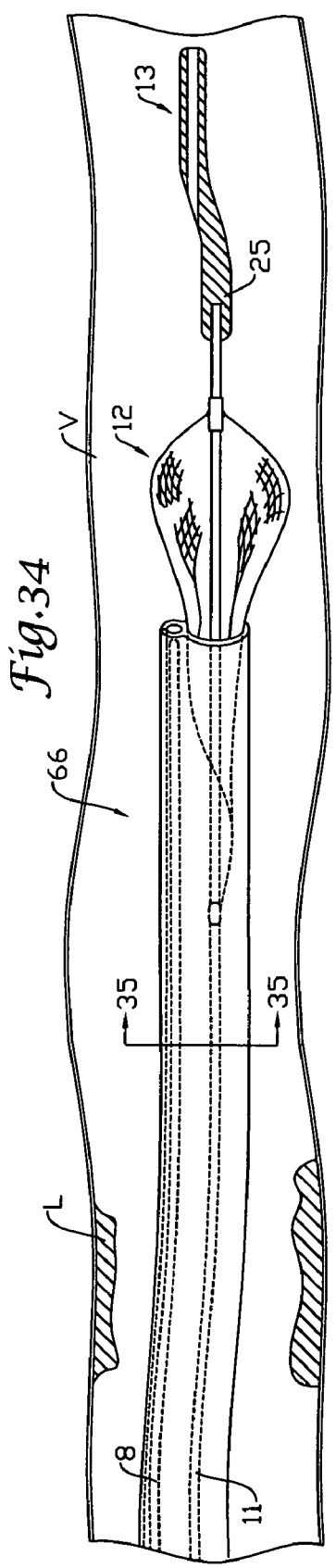

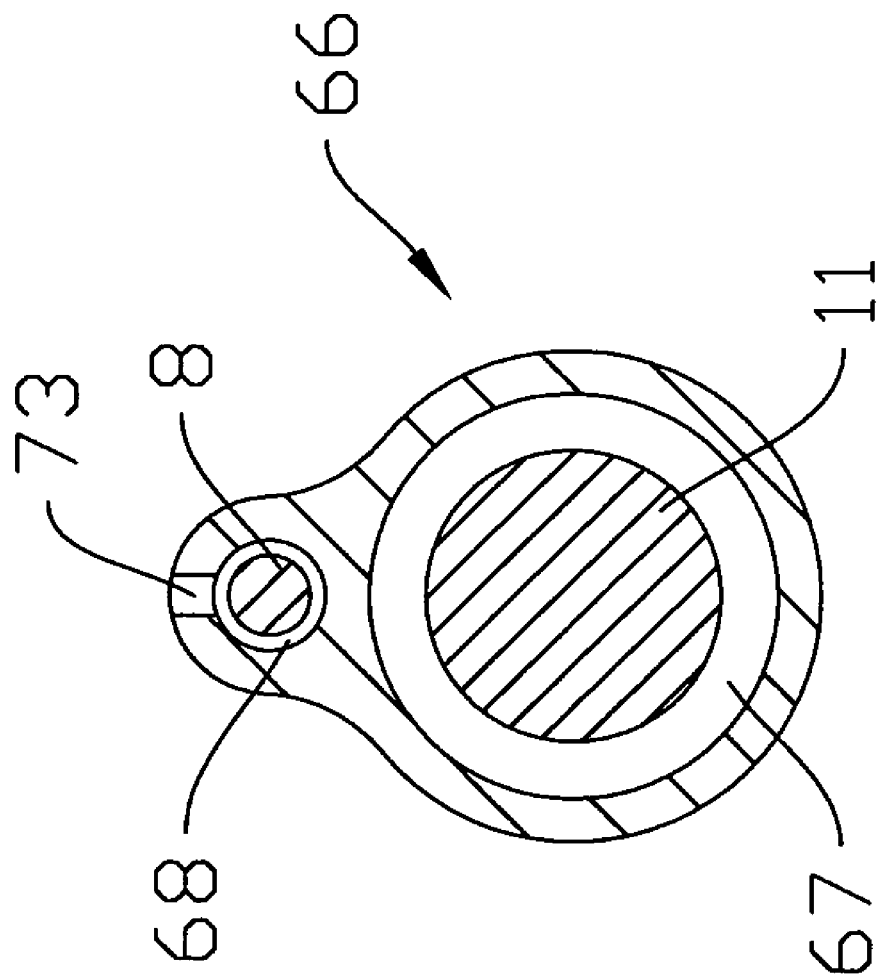

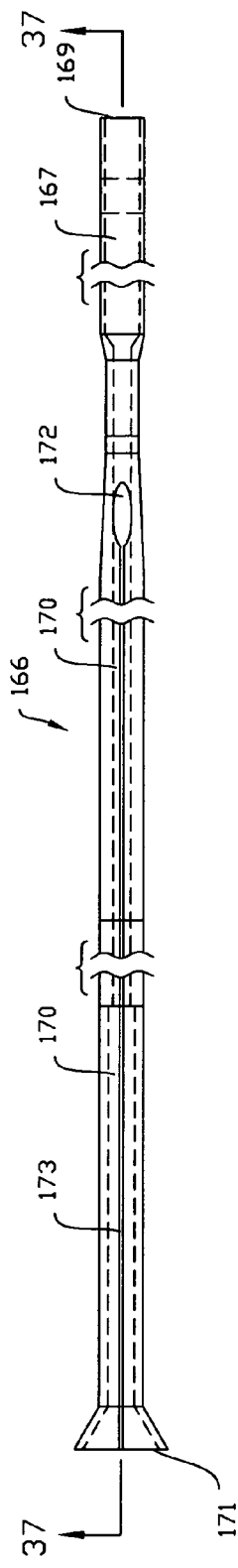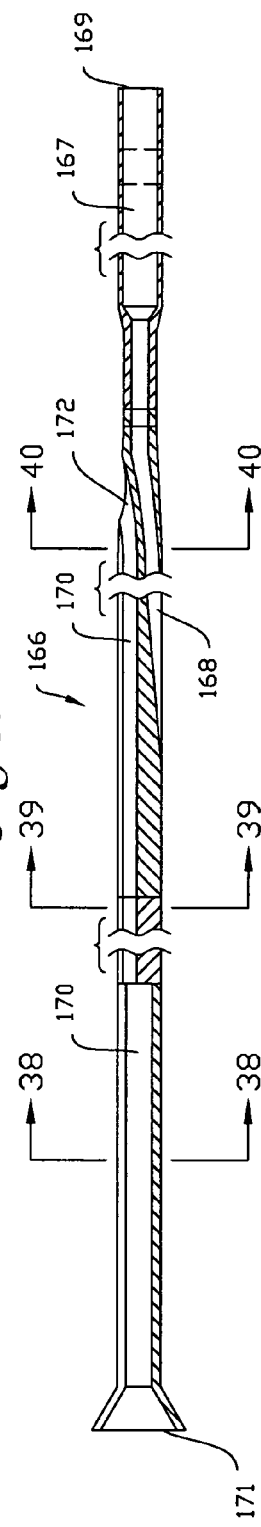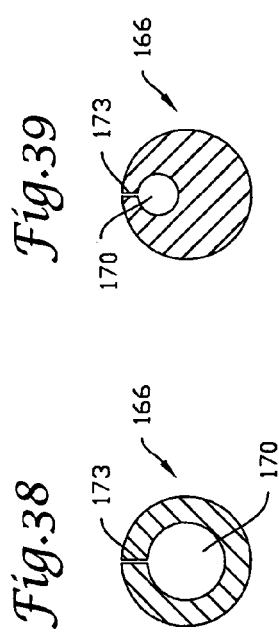

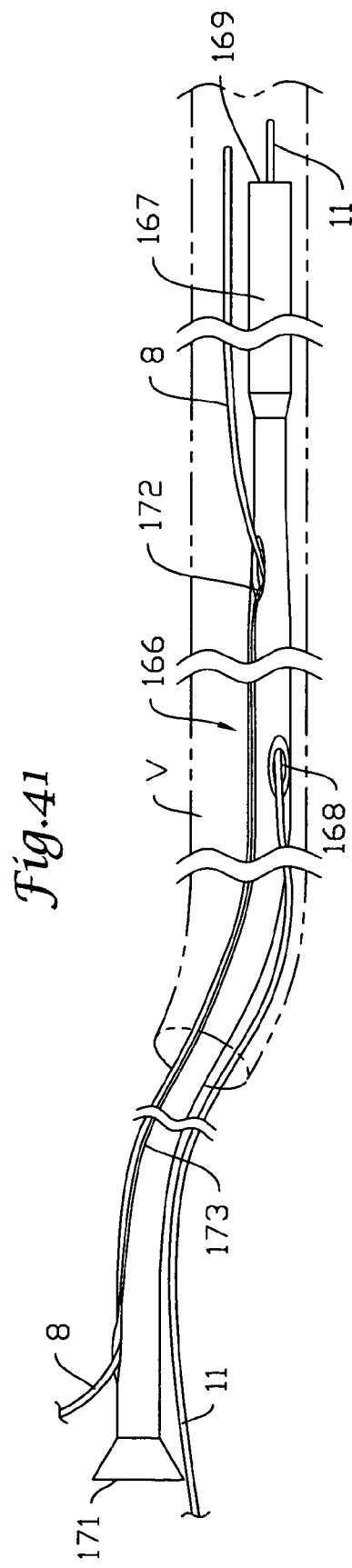

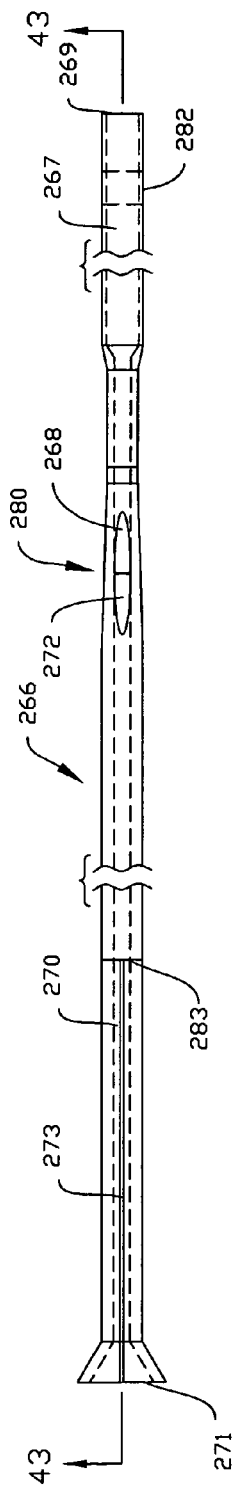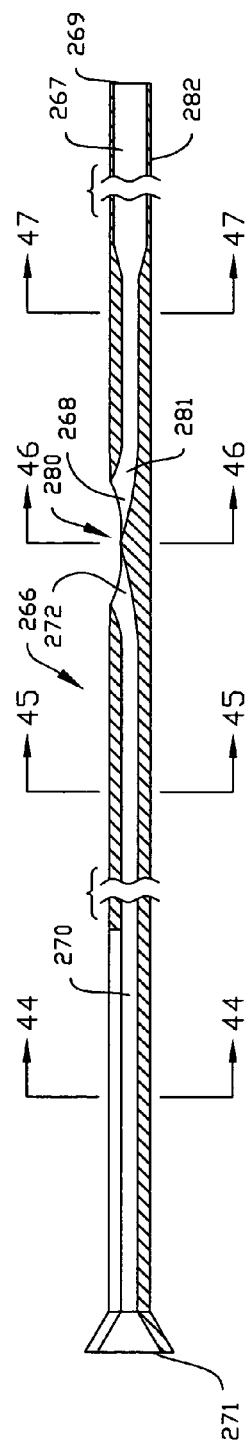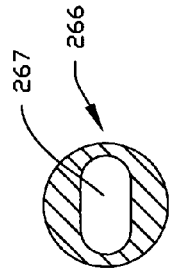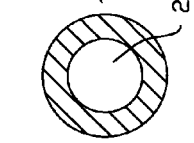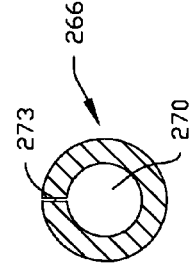

NOSE RIDER IMPROVEMENT FOR FILTER EXCHANGE AND METHODS OF USE

FIELD OF THE INVENTION

The present invention relates generally to the field of embolic protection devices. More specifically, the present invention pertains to systems and methods for transporting and exchanging intravascular devices within a body lumen.

BACKGROUND OF THE INVENTION

Guidewires are frequently used to advance intravascular devices to various locations within the body such as an artery or vein. Examples of therapeutic procedures employing such devices include percutaneous transluminal coronary angioplasty (PTCA), percutaneous extraction atherectomy, and stent placement. In a PTCA procedure, for example, a guidewire is percutaneously inserted into a patient's body, and then advanced to a target site where a stenosis or other occlusion is located. Once in place, an angioplasty catheter having an inflatable balloon is advanced along the guidewire and positioned across the site of the stenosis to be dilated. The inflatable balloon is then inflated, causing some embolic material to dislodge from the wall of the vessel and flow downstream.

To prevent the escape of embolic material dislodged during the therapeutic procedure, an embolic protection filter can be advanced to a location distal the target site and deployed to capture emboli present within the blood stream. These devices typically comprise a support structure coupled to a filter mesh or membrane that captures embolic material such as plaque and thrombus, while permitting the perfusion of blood through the vessel. The embolic protection filter may be configured to self-deploy within the vessel when actuated, and may be configured to radially collapse within a catheter or other delivery device to facilitate transport through the body.

During interventional vascular procedures such as angioplasty, atherectomy, thrombectomy and stenting, access to the lesion is often exacerbated due to the tortuous nature of the vasculature. To access the site of the lesion to be treated, the physician may advance an elongated wire such as a guidewire to a location within the vessel distal the lesion. Such guidewires are typically 0.014 inches in diameter, and vary in stiffness along their length. Since such guidewires often have a relatively small profile in comparison to other intravascular devices such as angioplasty catheters or stent delivery catheters, the ability to advance an intravascular device across the site of the lesion may be improved by using more conventional guidewires.

SUMMARY OF THE INVENTION

The present invention relates generally to the field of embolic protection devices. More specifically, the present invention pertains to systems and methods for transporting and exchanging intravascular devices within a body lumen. In one exemplary embodiment of the present invention, a filter system comprises a filter wire assembly and a filter delivery device. The filter wire assembly includes a guide tip and embolic protection filter disposed about an elongated wire. The guide tip has a proximal portion, a distal portion, and a guidewire lumen adapted to receive a guidewire. In certain embodiments, the embolic protection filter and guide tip can be formed on a single frame from one or more members and/or materials. The frame may include a coil or slotted tube, and may include a port configured to slidably receive a guidewire.

The guide tip may be tapered such that proximal portion has a relatively larger profile than the distal portion. In some embodiments, the guidewire lumen disposed within the guide tip may be substantially straight. In other embodiments, the guidewire lumen may include a curved region. In either embodiment, the guidewire lumen may include a polymeric coating to provide a smooth, lubricious interior surface for the guidewire. Moreover, the guide tip may include a radiopaque marker band, a spring coil, or an atraumatic distal tip, if desired.

A filter delivery device in accordance with an exemplary embodiment of the present invention may include an elongated tubular member extending distally to a distal sheath. A first lumen disposed within the distal sheath is adapted to receive the elongated wire. A second lumen disposed within the distal sheath is adapted to receive the guidewire.

The distal sheath may be dimensioned such that the proximal portion of the guide tip fits at least in part within the filter delivery device. In some embodiments, the distal sheath may include a key adapted to slide within a corresponding groove formed on the proximal portion of the guide tip. The key and groove ensure proper radial alignment of the guidewire lumen with the first lumen of the filter delivery device. In other embodiments, the shape of the guide tip and/or distal sheath can be configured to ensure proper radial alignment of the guidewire lumen with the first lumen.

The filter delivery device may include one or more skived regions located along the length of the distal sheath. These skived regions reduce the net frictional force exerted by the guidewire, and reduce the profile of the device to facilitate advancement through the vascular system. If desired, a loading tool can be used to thread the guidewire through the filter delivery device. A longitudinal slit spanning the length of the loading tool can be used to remove the loading tool from the skived region once the guidewire has been inserted into the guide tip and filter delivery device.

Once the filter wire assembly is loaded into the filter delivery device and advanced along the guidewire to a location distal a lesion, the guidewire can then be removed from the body. The filter delivery device can then be withdrawn proximally, causing the embolic protection filter to exit the distal sheath and expand within the vessel. A therapeutic device such as an angioplasty catheter can then be advanced along the filter wire to perform the therapeutic procedure. The embolic protection filter can then be collapsed and removed via a multiple-lumen retrieval sheath having a filter retrieval lumen and a guidewire lumen. If desired, a second guidewire contained in the retrieval sheath can be placed within the vessel. A longitudinal slit extending distally from the proximal end of the retrieval sheath can be used to remove the retrieval sheath from the second guidewire.

BRIEF DESCRIPTION OF THE DRAWINGS

FIG. 1 is a perspective view of a filter wire assembly in accordance with an exemplary embodiment of the present invention, wherein the filter wire assembly includes an embolic protection filter and guide tip attached to an elongated wire;

FIG. 2 is a cross-sectional view of the guide tip illustrated in FIG. 1, wherein the distal end of the elongated wire includes a protrusion configured to provide an interference fit with the guide tip;

FIG. 3 is a cross-sectional view of another guide tip in accordance with an exemplary embodiment of the present invention, wherein the guide tip includes a substantially straight guidewire lumen;

FIG. 4 is a cross-sectional view of the proximal portion of a guide tip in accordance with another exemplary embodiment of the present invention, wherein the guide tip includes a guidewire lumen having a curved region;

FIG. 5 is a partial cross-sectional view of a filter wire assembly in accordance with an exemplary embodiment of the present invention, wherein the filter and guide tip are formed on a single frame;

FIG. 6 is a partial cross-sectional view of a filter wire assembly in accordance with another embodiment of the present invention, wherein the filter frame includes a stopper mechanism;

FIG. 7 is a cross-sectional view showing the filter wire assembly of FIG. 6 along line 7-7;

FIG. 8 is a perspective view of a filter wire assembly in accordance with another exemplary embodiment of the present invention, wherein the filter frame and proximal support hoop comprise a single coil;

FIG. 9 is a perspective view of a filter frame in accordance with another exemplary embodiment of the present invention, wherein the filter frame includes a slotted tubular member;

FIG. 10 is a perspective view of a filter frame in accordance with another exemplary embodiment, wherein the filter frame includes a slotted tubular member having multiple slotted sections;

FIG. 11 is a perspective view of a filter frame in accordance with another exemplary embodiment, wherein the filter frame includes a slotted tubular member having multiple slotted sections;

FIG. 12 is a perspective of a filter frame in accordance with another exemplary embodiment, wherein the filter frame includes a slotted tubular member having a multiple slotted sections and a guidewire port;

FIG. 16 is a perspective view of the filter delivery device of FIG. 14, wherein the filter wire assembly of FIG. 1 is shown inserted through the delivery device;

FIG. 17 is a cross-sectional view of the filter system of FIG. 16, wherein the filter wire assembly is inserted at least in part within the distal sheath;

FIG. 18 is a cross-sectional view of a filter delivery system in accordance with another exemplary embodiment of the present invention, wherein the distal sheath includes a key configured to slide within a corresponding groove formed on the proximal portion of the guide tip;

FIG. 19 is another cross-sectional view showing the filter delivery system of FIG. 18 along line 19-19;

FIG. 20 is a perspective view of a filter delivery device in accordance with another exemplary embodiment of the present invention, wherein the filter delivery device includes a skived region;

FIG. 21 is a perspective view of a filter delivery device in accordance with yet another exemplary embodiment of the present invention having a skived region;

FIG. 22 is a perspective view of a filter delivery device in accordance with an exemplary embodiment of the present invention, wherein the filter delivery device includes several skived regions;

FIG. 23 is a perspective view of a loading tool in accordance with an exemplary embodiment of the present invention;

FIG. 24 is a cross-sectional view showing the loading tool of FIG. 23 along line 24-24;

FIG. 25 is another perspective view of the loading tool of FIG. 23, wherein the loading tool is shown inserted into the guide tip and filter delivery device;

FIG. 26 is yet another perspective view of the loading tool of FIG. 23, wherein the loading tool is inserted into the guide tip and filter delivery device, and the guidewire is inserted through the device;

FIG. 27 is a perspective view of loading tool of FIG. 23, wherein the loading tool is shown being removed from the guidewire;

FIG. 28 is a perspective view of a loading member in accordance with an alternative embodiment of the present invention, wherein the loading member is placed across a skived region on the filter delivery device;

FIG. 29 is a plan view of a guidewire inserted into a vessel at a location distal a lesion;

FIG. 30 is a plan view of a filter delivery device and filter wire assembly advanced to the distal portion of the guidewire illustrated in FIG. 29;

FIG. 31 is a plan view of the filter delivery system of FIG. 30, wherein the guidewire has been withdrawn;

FIG. 32 is another plan view of the filter system of FIG. 30, wherein the filter delivery device has been withdrawn, and wherein the embolic protection filter is in a deployed state;

FIG. 33 is a plan view illustrating a therapeutic device advanced along the filter wire to the site of the lesion;

FIG. 34 is a plan view illustrating a retrieval sheath in accordance with an exemplary embodiment of the present invention, wherein the retrieval sheath contains a second guidewire, and wherein the embolic protection filter is collapsed at least in part within the retrieval sheath;

FIG. 35 is a cross-sectional view showing the retrieval sheath of FIG. 34 along line 35-35;

FIG. 36 is a perspective view of a retrieval sheath in accordance with another exemplary embodiment of the present invention, wherein the retrieval sheath includes an opening for single operator exchange of the second guidewire;

FIG. 37 is a cross-sectional view showing the retrieval sheath of FIG. 36 along line 37-37;

FIG. 38 is a cross-sectional view showing the retrieval sheath of FIG. 37 along line 38-38;

FIG. 39 is a cross-sectional view showing the retrieval sheath of FIG. 37 along line 39-39;

FIG. 40 is a cross-sectional view showing the retrieval sheath of FIG. 37 along line 40-40;

FIG. 41 is a view of the retrieval sheath illustrated in FIGS. 36-40, wherein the retrieval sheath is shown advanced to a desired location within a body lumen, and wherein the retrieval sheath is loaded with a second guidewire;

FIG. 42 is a perspective view of a retrieval sheath in accordance with another exemplary embodiment of the present invention configured for single operator exchange;

FIG. 43 is a cross-sectional view showing the retrieval sheath of FIG. 42 along line 43-43;

FIG. 44 is a cross-sectional view showing the retrieval sheath of FIG. 43 along line 44-44;

FIG. 45 is a cross-sectional view showing the retrieval sheath of FIG. 43 along line 45-45;

FIG. 46 is a cross-sectional view showing the retrieval sheath of FIG. 43 along line 46-46; and FIG. 47 is a cross-sectional view showing the retrieval sheath of FIG. 47 along line 47-47.

DETAILED DESCRIPTION OF THE INVENTION

Figure 13:
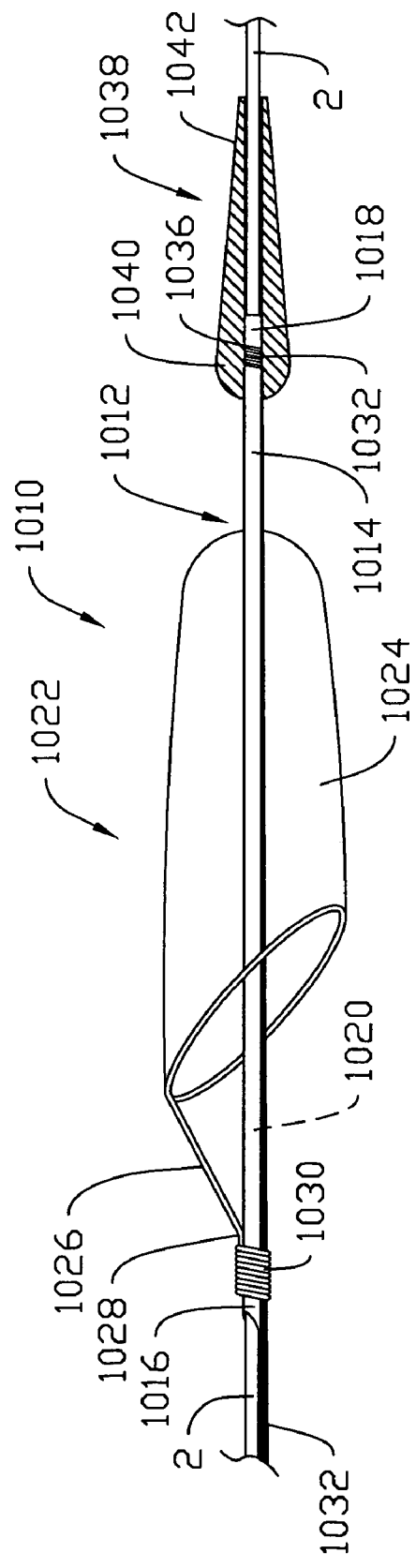
FIG. 13 is a partial cross-sectional view of a filter wire assembly in accordance with another embodiment of the present invention.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, materials and manufacturing processes are illustrated for the various elements, those skilled in the art will recognize that many of the examples provided have suitable alternatives that may be utilized.

FIG. 1 is a perspective view of a filter wire assembly 10 in accordance with an exemplary embodiment of the present invention. Filter wire assembly 10 includes an elongated wire 11, an embolic protection filter 12, and a guide tip 13. Elongated wire 11 has a proximal end 14 and a distal end 15. As is discussed in greater detail below, filter wire assembly 10 is adapted to attach to a filter delivery device which, in turn, can be utilized to transport the filter wire assembly 10 to a desired location within a patient's body.

Elongated wire 11 can be constructed of any suitable material(s) biocompatible with the body. Examples of such materials include 304 or 316 grade stainless steel, platinum, or nickel-titanium alloy (Nitinol). Nickel-titanium alloy exhibits super-elastic capabilities at body temperature (approximately 37° C.), which permits substantial bending or flexing with a relatively small amount of residual strain. It is contemplated, however, that other materials can be used. For example, in some embodiments, elongated wire 11 may comprise a stainless steel core wire surrounded by a polymeric coating to facilitate smooth transport of other intravascular devices thereon.

The embolic protection filter 12 may include a filter mesh or membrane 16 operatively coupled to a wire 17 that forms a suspension arm 18 and a support hoop 19. The wire 17 may comprise a shape-memory material such as a nickel-titanium alloy, allowing the support hoop 19 to bend and flex while maintaining its original shape.

A radiopaque coil 20 helically disposed about the support hoop 19 can be used to fluoroscopically judge the placement and deployment status of the embolic protection filter 12 within the patient. Coil 20 may be formed of a relatively high radiopaque material such as gold, platinum or tantalum, which can be utilized in conjunction with a fluoroscopic monitor to determine an accurate measure of the location of the embolic protection filter 12 within the vasculature.

The proximal end 21 of wire 17 can be attached to a first tubular member 22 disposed about the elongated wire 11, as shown in FIG. 1. Alternatively, the proximal end 21 of wire 17 can be attached directly to the elongated wire 11. Attachment of wire 17 to either the first tubular member 22 or directly to elongated wire 11 can be accomplished by any suitable attachment means such as adhesive, brazing, soldering, welding, crimping or any combination(s) thereof.

In the embodiment illustrated in FIG. 1, embolic protection filter 12 is further coupled at a distal section 23 to a second tubular member 24 slidably and rotationally disposed about elongated wire 11 distal the first tubular member 22. Second tubular member 24 has an inner diameter slightly larger than the outer diameter of the elongated wire 11, allowing the second tubular member 24 to move thereon. In an alternative embodiment (not shown), the distal section 23 of embolic protection filter 12 can be attached directly to the elongated wire 11. When attached directly to the elongated wire 11, the distal section 23 of embolic protection filter 12 is substantially prevented from moving along the elongated wire 11.

Filter wire assembly 10 may further include a guide tip 13. Guide tip 13 has a proximal portion 25, a distal portion 26, and a guidewire lumen 27 therethrough. Guidewire lumen 27 may include a polymeric liner such as polytetrafluoroethylene (PTFE) to provide a smooth, lubricious interior surface for a second wire.

As shown in FIG. 1, the distal end 15 of elongated wire 11 may be attached to the proximal portion 25 of guide tip 13 at joint 28. Elongated wire 11 can be attached to the guide tip 13 at joint 28 by, for example, molding the proximal portion 25 of guide tip 13 over the distal end 15 of elongated wire 11. Alternatively, elongated wire 11 can be attached to guide tip 13 by means of a shrink-fit, adhesive, soldering, welding, crimping, or other suitable attachment means.

In one exemplary embodiment illustrated in FIG. 2, the distal end 15 of elongated wire 11 may include attachment means configured to provide an interference fit with joint 28 of guide tip 13. The attachment means may comprise a coil 29 disposed about the distal end 15 of the elongated wire 11 having an outer diameter that is slightly larger than the inner diameter of the joint 28. Elongated wire 11 can be attached to the proximal portion 25 of guide tip 13 by advancing the distal end 15 into joint 28 with sufficient force to overcome the interference fit. A reduced inner diameter portion 30 on the joint 28 prevents the distal end 15 of elongated wire 11 from detaching from the guide tip 13 once the distal end 15 of the elongated wire 11 is inserted into the joint 28.

Guide tip 13 is further configured in size and shape to facilitate advancement of the filter wire assembly 10 through the patient's body. For example, in the exemplary embodiment illustrated in FIG. 2, the guide tip 13 includes a tapered profile such that the proximal portion 25 of guide tip 13 has a larger profile than the distal portion 26 of guide tip 13.

Referring now to FIG. 3, a guide tip 113 in accordance with an alternative embodiment of the present invention will now be described. Guide tip 113 includes a proximal portion 125, a distal portion 126, and a guidewire lumen 127. Guide tip 113 has a tapered profile such that the proximal portion 125 of guide tip 113 is relatively larger than the distal portion 126 of guide tip 113. The guidewire lumen 127 of guide tip 113 is substantially straight, extending distally from a port 131 disposed on the proximal portion 125 of the guide tip 113 to a port 132 disposed on the distal portion 126 of guide tip 113. As with the previous embodiment, guidewire lumen 127 is adapted to receive a guidewire therethrough.

A tapered hole 133 disposed on the proximal portion 125 of guide tip 113 can be used to attach the distal end 15 of elongated wire 11 to the proximal portion 125 of guide tip 113. Tapered hole 133 includes a tapered inner diameter that facilitates insertion of the distal end 15 of elongated wire 11 into tapered hole 133. The proximal portion 125 of guide tip 113 can be crimped to attach the elongated wire 11 to the guide tip 113, and, if desired, may be set with an adhesive, solder or other attachment means.

Guide tip 113 further includes a radiopaque marker band 134 placed on the distal portion 126 of guide tip 113. Radiopaque marker band 134 includes a radiopaque material (e.g. platinum, gold, tantalum, tungsten, etc.) that can be used by the operator to fluoroscopically judge the location of the guide tip 113 when placed within the vasculature.

The distal portion 126 of guide tip 113 may also be spring-loaded in order to provide greater flexibility and steering during transport within the body. A spring coil 135 can be formed integral with the distal portion 126 of guide tip 113, or can be helically wound about the distal portion 126 of the guide tip 113. If desired, spring coil 135 may be formed of a radiopaque material to act as a radiopaque marker, either alone or in combination with radiopaque marker band 134.

To reduce tissue damage during placement, the distal portion 126 of guide tip 113 may further include an atraumatic distal tip 136. Distal tip 136 may include a relatively soft, atraumatic material (e.g. a low-absorption thermal plastic) that is adapted to deform when compressed against the wall of the vessel. This deformation prevents the guide tip 113 from penetrating the vessel wall.

In another exemplary embodiment illustrated in FIG. 4, a guide tip 213 in accordance with the present invention may include a guidewire lumen 227 having a curved portion 237. As shown in FIG. 4, guidewire lumen 227 extends from the distal end (not shown) on the guide tip 213 proximally to a point located on the proximal portion 225 of guide tip 213. At portion 237, the guidewire lumen 227 curves slightly, terminating at port 231. As with the embodiment illustrated in FIG. 3, guide tip 213 may include a tapered hole 233 for insertion of the distal end 15 of elongated wire 11, and may include a radiopaque marker band, spring coil and/or atraumatic distal tip.

FIG. 5 is a partial cross-sectional view of a filter wire assembly 310 in accordance with an exemplary embodiment of the present invention, wherein the embolic protection filter 312 and guide tip 313 are formed on a single frame 338. Frame 338 comprises proximal section 339, a middle section 340, and a distal section 341. Frame 338 further defines an inner lumen 327 configured to slidably receive a second guidewire 2 through a port 342. The proximal section 339 of frame 338 can be mounted to the distal end 15 of elongated wire 11.

The distal section 341 of frame 338 has an enlarged outer diameter, forming a guide tip 313. Guide tip 313 includes a proximal portion 325 and a distal portion 326. The guide tip 313 is tapered such that the proximal portion 325 of guide tip 313 is larger than the distal portion 326 of guide tip 313. In use, guide tip 313 is configured in size and shape to facilitate advancement of the filter wire assembly 310 through the vasculature.

The frame 338 can be formed from an injection mold process utilizing a suitable polymeric material such as polypropylene (PP) or polyvinylchloride (PVC). In other embodiments, the frame 338 may be formed from different members and/or materials that are coupled together. For example, the proximal and distal sections 339,341 of frame 338 may be formed of a polymeric member, whereas the middle section 340 of frame 338 may comprise a coil or slotted hypotube. The various sections of the frame 338 can be bonded together by adhesive, welding, crimping, soldering, insert molding, or other suitable bonding technique.

FIG. 6 is a partial cross-sectional view of a filter wire assembly 410 in accordance with another exemplary embodiment of the present invention, wherein the filter frame 438 includes a stopper mechanism 474. Similar to the embodiment illustrated in FIG. 5, the embolic protection filter 412 and guide tip 413 are formed on a single frame 438 having an inner lumen 427 configured to slidably receive a second guidewire 2. The proximal section 439 of filter frame 438 may be formed integral with the distal end 15 of the elongated wire 11, as shown in FIG. 6, or can be formed as separate elements similar to that depicted in FIG. 5. Visual indicator means such as a spiral-shaped stripe 475 may be employed to permit the user to visually differentiate between the elongated wire 11 and the guidewire 2.

The guide tip 413 may be tapered such that the proximal portion 425 of guide tip 423 is larger than the distal portion 426 of guide tip 413. In use, the embolic protection filter 412 and guide tip 413 are configured to fit within a delivery sheath 476 for transport through the patient's body. As shown in FIG. 7, the delivery sheath 476 may include a longitudinal slit 477 along its length allowing the operator to peel-away the delivery sheath 476 from the filter wire assembly 410 once placed at the target site.

Stopper mechanism 474 may include an object attached to the filter frame 438 configured to prevent the user from retracting the filter wire assembly 410 beyond a necked-down section 478 of the delivery sheath 476. As shown in FIG. 6, stopper mechanism 474 may include, for example, a wire coil 479 having an outer diameter slightly larger than the inner diameter of the delivery sheath 476 at the necked-down section 478. In use, the wire coil 479 prevents proximal movement of the filter wire assembly 410 beyond the necked-down section 478 of the delivery sheath 476.

FIG. 8 is a perspective view of a filter wire assembly 510 in accordance with another exemplary embodiment of the present invention, wherein the filter frame 538 and support hoop 519 are formed of a single coil. Filter frame 538 has a proximal section 539, a distal section 541, and an inner lumen (not shown) configured to slidably receive a guidewire 2. The distal section 541 of filter frame 538 is attached to a guide tip 513 to facilitate advancement of the filter 512 through the vasculature.

The coiled frame 538 may be formed of a metal or metal alloy such as stainless steel or nickel-titanium alloy. The specifications (e.g. wire pitch, inner diameter, outer diameter, length, etc.) of the frame 538 can be selected to accommodate to the type of guidewire or filter employed, and the particular location of the body to be traversed.

FIGS. 9-12 depict other selected embodiments of the present invention wherein the filter frame includes a slotted tubular member. As shown in FIG. 9, for example, the slotted tubular member 638 may include a hypotube having a continuous slot or groove 642 helically disposed about a portion of the outer surface of the tubular member 538. The angle, pitch, and width of the slots can be selected to impart a particular flexibility to the tubular member 638, if desired.

In another embodiment illustrated in FIG. 10, a slotted tubular member 738 in accordance with the present invention may include multiple sections having differing flexibility characteristics. Tubular member 738 may include a first region 739 having loosely spaced slots 742, a second region 740 distal the first region 739 having slots 742 spaced narrower than at the first region 739, and a third region 741 distal the second region 740 having slots 742 spaced narrower than at the first and second regions 739,740. In use, the three regions 739,740,741 impart variable flexibility along the length of the tubular member 738.

The location and number of regions can be varied depending on the particular performance characteristics desired. For example, in one exemplary embodiment illustrated in FIG. 11, the slotted tubular member 838 may include a first region 839 having a loosely spaced slots 842, a third region 841 having tightly spaced slots 842, and a second region 840 having slots 842 that are more loosely spaced than the slots at the first and third regions 839,841. The arrangement of the three regions 839,840,841 provides a stiffer flexural profile in the middle portion of the tubular member 838.

In certain embodiments, the tubular member 938 may include a port 942, such as that depicted in FIG. 12. The port 942 may be configured to slidably receive a guidewire through the inner lumen of the tubular member 938, similar to that described above with respect to FIG. 7.

FIG. 13 is a partial cross-sectional view of a filter wire assembly 1010 in accordance with another exemplary embodiment of the present invention. Filter wire assembly 1010 comprises a filter frame 1012 including a tubular member 1014 with a proximal end 1016, a distal end 1018, and an inner lumen therethrough 1020 configured to slidably receive a second guidewire 2. The filter frame 1012 may be configured to support an embolic protection filter 1022 including a filter membrane 1024 and a support strut 1026. The proximal end 1028 of the support strut 1026 may be coupled to the tubular member 1014 via a coil 1030 that can be slid over the outer portion of the tubular member 1014 and secured thereto with solder, adhesive or other suitable bonding technique.

An elongated wire 1032 secured to the tubular member 1014 may be used to guide the filter wire assembly 1010 within the body. The elongated wire 1032 can be secured to the tubular member 1014 at one or more attachment locations. As shown in FIG. 13, for example, the elongated wire 1032 may be coupled to the tubular member 1014 via coil 1030. The elongated wire 1032 may also be secured at or near its distal end 1034 to a second coil 1036 placed about the distal end 1018 of the tubular member 1014. In certain embodiments such as that depicted in FIG. 13, the elongated wire 1032 may taper in the distal direction to increase the flexibility at the distal end 1034, if desired.

The distal end 1018 of the tubular member 1014 may be coupled to an atraumatic guide tip 1038. Guide tip 1038 includes a proximal portion 1040 and a distal portion 1042. The guide tip 1038 is tapered such that the proximal portion 1040 of the guide tip 1038 is larger than the distal portion 1042 of the guide tip 1038. As with other embodiments described herein, the guide tip 1038 may be configured in size and shape to facilitate advancement of the filter wire assembly 1010 through the vasculature.

Figure 14:
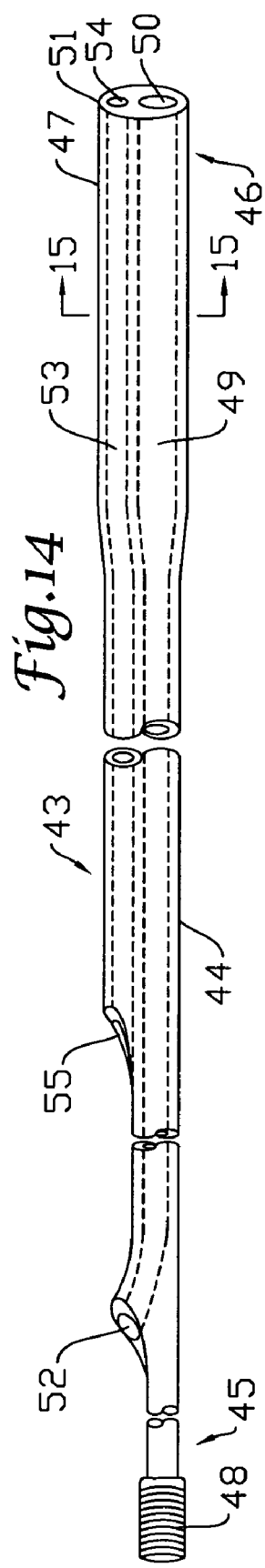
FIG. 14 is a perspective view of a filter delivery device in accordance with an exemplary embodiment of the present invention.

Referring now to FIG. 14, a filter delivery device 43 in accordance with an exemplary embodiment of the present invention will now be described. Filter delivery device 43 comprises an elongated tubular member 44 having a proximal section 45 and a distal section 46. The distal section 46 of elongated tubular member 44 is flared slightly, forming a distal sheath 47 that is configured to contain an embolic protection filter such as that described with respect to FIG. 1. The proximal section 45 of elongated tubular member 44 includes a handle 48 that can be used by the operator to maneuver the filter delivery device 43 through the patient's vasculature.

Elongated tubular member 44 defines a first lumen 49 adapted to receive a wire at a first port 50 located at the distal end 51 of the distal sheath 47. The first lumen 49 extends proximally from first port 50 through the distal sheath 47, and exits the elongated tubular member 44 at a first exit port 52.

Figure 15:
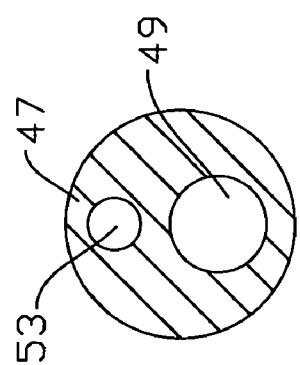
FIG. 15 is a cross-sectional view showing the filter delivery device of FIG. 14 along line 15-15.

Elongated tubular member 44 further defines a second lumen 53 adapted to receive a wire at a second port 54 located at the distal end 51 of the distal sheath 47. The second lumen 53 extends proximally from second port 54 through the distal sheath 47, and exits the elongated tubular member 44 at a second exit port 55 disposed distal the first exit port 52. As shown in greater detail in FIG. 15, the portion of first lumen 49 disposed within distal sheath 47 is substantially circular in shape, and is adapted to receive, in part, an embolic protection filter. The second lumen 53 is also substantially circular in shape, and is adapted to receive a wire.

To load the filter wire assembly 10 into the filter delivery device 43, the operator inserts the proximal end 14 of elongated wire 11 into first port 50, and advances the elongated wire 11 through first lumen 49 until the proximal end 14 of elongated wire 11 exits the first exit port 52, as shown in FIG. 16. To collapse the embolic protection filter 12 into the distal sheath 47, the operator continues to feed the elongated wire 11 proximally through the first lumen 49 until the embolic protection filter 12 and a portion of the guide tip 13 are loaded into the distal sheath 47, as shown in FIG. 17. Once the embolic protection filter 12 and guide tip 13 are collapsed and loaded at least in part into the distal sheath 47, the operator may, if necessary, align the guidewire lumen 27 of guide tip 13 concentrically with the second lumen 53 of the filter delivery device 43 such that a portion of the guidewire within the second lumen is generally coplanar with a portion of the guidewire within the guidewire lumen of the guide tip.

In one exemplary embodiment illustrated in FIG. 18, the distal sheath 147 may include a key 156 configured to slide within a corresponding groove 57 formed on the proximal portion 25 of the guide tip 13. As shown in cross-section in FIG. 19, the key 156 may be configured in size and shape to permit the proximal portion 25 of guide tip 13 to slide within the distal sheath 147 when radially aligned with groove 57. When utilized, the key 156 and groove 57 ensure radial alignment of the guidewire lumen 27 and second lumen 153 to facilitate insertion of a guidewire therethrough. Moreover, the key 156 and groove 57 may be utilized to prevent radial displacement of the guide tip 13 relative to the distal sheath 147 during placement of the device within the body.

It is to be understood that while a key and groove are utilized in the exemplary embodiment of FIGS. 18-19, other configurations are possible to ensure radial alignment of the guidewire lumen of the guide tip with the second lumen of the filter delivery device. For example, the proximal portion of the guide tip may include a flat, forming a D-shaped configuration (when viewed from an end) configured to slide within a corresponding flat formed within the distal sheath. In use, the D-shaped configuration permits insertion of the guide tip into the distal sheath when the guidewire lumen of the guide tip is aligned with the second lumen of the filter delivery device.

It is to be further understood that while both the first and second lumens 49, 53 of elongated tubular member 44 are shown extending through the entire length of the distal sheath 47, other configurations have been envisioned. For example, as shown in FIGS. 20-21, the second port 254, 354 of filter delivery device 243, 343 may terminate at various locations proximal the distal end 251, 351 of the distal sheath 247, 347, forming skived regions 258, 358. These skived regions 258, 358 reduce the net frictional force exerted on the guidewire 11, reduce the crossing profile of the device, and in some embodiments, allow the guide tip 13 to rotate relative to the distal sheath 247, 347 while permitting the guidewire 11 to freely slide through the device.

In one exemplary embodiment shown in FIG. 22, the filter delivery device 443 may include several collars 459 that form a plurality of skived regions 458 along the length of the elongated tubular member 444. As with the exemplary embodiments illustrated in FIGS. 20-21, the skived regions 458 reduce the frictional force exerted on the guidewire 11, reduce the crossing profile in certain areas along the device 443, and permit the device 443 to bend or flex when advanced through the patient's body.

To thread the guidewire 11 through each skived region, an optional loading tool 60 may be used. As shown in FIGS. 23-27, a loading tool 60 in accordance with the present invention may include an elongated tubular member 61 configured to slide within the guidewire lumen of the guide tip and the second lumen of the filter delivery device. Loading tool 60 has a proximal end 62, a distal end 63, and an inner lumen 64 configured to slidably receive the elongated wire 11. A longitudinal slit 65 extends along the entire length of the elongated tubular member 61. The distal end 63 of loading tool 60 is flared slightly to facilitate insertion of the elongated wire 11 into the inner lumen 64.

In use, loading tool 60 can be used to insert the elongated wire 11 through any of the aforementioned filter delivery devices and guide tips. As illustrated in FIGS. 25-27, for example, loading tool 60 can be used to insert elongated wire 11 into the guide tip and filter delivery device combination described with respect to FIG. 20. To insert the loading tool 60 into the guide tip 13 and filter deliver device 243, the operator threads the proximal end 62 of the elongated tubular member 61 into guide lumen 27 of guide tip 13, and advances the loading tool 60 across the skived region 258 until the proximal end 62 of the loading tool 60 is disposed within the second lumen 253 of the filter delivery device 243, as shown in FIG. 25. Once the loading tool 60 is loaded into the guide tip 13 and filter delivery device 243, the proximal end 14 of the elongated wire 11 is then inserted into the inner lumen 64 of elongated tubular member 61 at the flared distal end 63, and advanced until the proximal end 14 of the elongated wire 11 is located beyond the proximal end 62 of the elongated tubular member 61, as shown in FIG. 26. Once the guidewire 11 has been advanced through the elongated tubular member 61, the loading tool 60 can then be withdrawn from the filter delivery device 243 and guide tip 13. As shown in FIG. 27, the elongated wire 11 can be removed from the loading tool 60 vis-à-vis the longitudinal slit 65 located on the elongated tubular member 61. A stylet (not shown) can then be inserted through the inner lumen 64 of elongated tubular member 61 to keep the loading tool 60 stiff for subsequent use.

In an alternative embodiment illustrated in FIG. 28, a loading tool 160 in accordance with another exemplary embodiment of the present invention may include a tube segment 161 having longitudinal slit 165 thereon. The length of the tube segment 161 is approximately equal to the length of the skived region 258 such that the loading tool 160 can be temporarily placed across the skived region 258. In use, the loading member 160 allows the operator to more easily thread the elongated wire 11 from the skived region 258 into the second lumen 253 of the filter delivery device 243. The longitudinal slit 165 spans the entire length of the tube segment 161, allowing the operator to later remove the loading tool 160 from the skived region 258, if desired.

Methods of using the filter exchange devices of the present invention will now be described in the context of an interventional procedure such as percutaneous transluminal coronary angioplasty (PTCA). In practicing the subject invention, a conventional guidewire 2 having a proximal end (not shown) and a distal end 4 is percutaneously inserted into a patient, and advanced to a desired location within a vessel V distal a lesion L, as shown in FIG. 29. Once in place, the filter wire assembly 10 is loaded into the filter delivery device 43, and, if necessary, aligned such that the guidewire lumen 27 of the guide tip 13 is radially aligned with the second lumen 53 of the filter delivery device 43. Once assembled, the operator next inserts the proximal end of the guidewire 2 through the guidewire lumen 27 and second lumen 53, and advances the filter wire assembly 10 and filter delivery device 43 to a location at or near the distal end 4 of the guidewire 2, as shown in FIG. 30.

Once the filter delivery device 43 and filter wire assembly 10 are in position distal lesion L, guidewire 2 can then be withdrawn from the filter delivery device 43 and guide tip 13, and removed from the vessel, as shown in FIG. 31. To deploy the embolic protection filter 12 within the vessel V, the operator, while holding the elongated wire 11 stationary, retracts the elongated tubular member 44 proximally, causing the embolic protection filter 12 to exit the first lumen 49 and radially deploy within the vessel V, as shown in FIG. 32. An interventional device such as an angioplasty catheter 6 can then be advanced along the elongated wire 11 and inflated, causing some of the emboli E to dislodge from the vessel wall and flow downstream, as illustrated in FIG. 33.

To retrieve the filter wire assembly 10 from vessel V, a multiple-lumen retrieval sheath 66 containing a second guidewire 8 can be advanced along the elongated wire 11 to retrieve the embolic protection filter 12. As shown in FIG. 34, the second guidewire 8 can be advanced within the vessel V to the same location of the elongated wire 11 used to transport the filter delivery device 43 and filter wire assembly 10. As shown in cross-section in FIG. 35, retrieval sheath 66 includes a first lumen 67 adapted to receive elongated wire 11, embolic protection filter 12, and the proximal portion 25 of the guide tip 13. A second lumen 68 disposed within the retrieval sheath 66 is adapted to receive the second guidewire 8. A longitudinal slit 73 extending distally from the proximal end of retrieval sheath 66 allows the retrieval sheath 66 to be removed from the second guidewire 8.

In an alternative embodiment illustrated in FIGS. 36-41, a multiple-lumen retrieval sheath 166 may be configured to permit single operator exchange of filter wire assembly 10 with the second guidewire 8 within the body. Retrieval sheath 166 includes a first lumen 167 adapted to receive, for example, the elongated wire 11, embolic protection filter 12, and the proximal portion 25 of guide tip 13 described above with respect to FIG. 1. The first lumen 167 extends distally from a first port 168 to the distal end 169 of the retrieval sheath 166. A second lumen 170 extends from the proximal end 171 of the retrieval sheath 166 to a second port 172 disposed on the retrieval sheath 166. The location of port 172 can be either proximal the distal end 169 of the retrieval sheath 166, as shown in FIGS. 36-37, or can be located at the distal end 169 of the retrieval sheath 166 (not shown). A longitudinal slit 173 extending along the entire length of the second lumen 170 is configured to allow the retrieval sheath 166 to be removed from the second guidewire 8.

To retrieve the filter wire assembly 10 from the body, the proximal end 14 of the elongated wire 11 is inserted into the first lumen 167 at the distal end 169 of the retrieval sheath 166, and is then advanced proximal the first port 168. Holding the elongated wire 11 stationary, the operator next advances the retrieval sheath 166 over the elongated wire 11 to capture the filter wire assembly 10 within the first lumen 167. The second guidewire 8 can be loaded into the second lumen 170 of the retrieval sheath 166, and advanced to a desired location within vessel V. The retrieval sheath 166 can then be removed from the patient's body by pulling the second guidewire 8 through the longitudinal slit 173 and holding second guidewire 8 steady while withdrawing the retrieval sheath 166 and filter wire assembly 10 from the vessel, as shown in FIG. 41.

In an alternative embodiment illustrated in FIGS. 42-47, a multiple-lumen retrieval sheath 266 configured for single operator exchange of a filter wire assembly (e.g. filter assembly 10) may include a first lumen 267 adapted to receive, for example, the elongated wire 11, embolic protection filter 12, and guide tip 13 described above with respect to FIG. 1. The first lumen 267 may extend distally from a first port 268 to the distal end 269 of the retrieval sheath 266. The first port 268 may be formed by removing a portion of the outer wall of the retrieval sheath 266, creating a groove 280 in the retrieval sheath 266 that exposes an offset portion 281 of the first lumen 267. As shown in FIG. 47, the portion of first lumen 267 extending from the first port 268 to a flared distal sheath 282 may have a substantially rectangular shape with rounded edges. At the flared distal sheath 282, the inner diameter of the first lumen 267 assumes a substantially circular shape configured to receive the embolic protection filter 12 and a portion of the guide tip 13.

A second lumen 270 extending from the proximal end 271 of the retrieval sheath 266 to a second port 272 disposed on the retrieval sheath 266 proximal the first port 268 may be configured to receive an exchange wire such as second guidewire 8 described herein. A longitudinal slit 273 extending distally from the proximal end 271 of the retrieval sheath 266 to a location 283 proximal the second port 272 may be configured to permit the retrieval sheath 266 to be removed from the second guidewire 8 in a manner similar to that described above with respect to FIG. 41.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. Changes may be made in details, particular in matters of size, shape, and arrangement of parts without exceeding the scope of the invention. It will be understood that this disclosure is, in many respects, only illustrative.

What is claimed is:

1. A filter system comprising:
    a guide tip having a proximal portion and a distal portion, the guide tip defining a guidewire lumen therethrough adapted to receive and slidably pass a guidewire;
    an elongated wire having a proximal end and a distal end, the distal end of said elongated wire attached to the proximal portion of said guide tip at a point of attachment;
    an embolic protection filter disposed along the elongated wire;
    an elongated tubular member extending distally to a distal end defining a distal sheath, the elongated tubular member defining a first lumen, having a proximal and a distal end, adapted to receive the elongated wire and a second, generally parallel lumen having proximal and distal ports, adapted to receive the guidewire; wherein, when the guidewire is present in use, the embolic protection filter is collapsible at least in part within the distal sheath, further wherein, when the embolic protection filter is collapsed in part within the distal sheath, a portion of the guidewire within the second lumen of the elongated tubular member adjacent the distal port of the second lumen is generally coplanar with a portion of the guidewire within the guidewire lumen of the guide tip, a portion of the elongated wire within the first lumen of the elongated tubular member adjacent the distal end of the first lumen, and the point of attachment of the elongated wire to the guide tip.

2. The filter system of claim 1, wherein the guide tip has a tapered profile.

3. The filter system of claim 1, wherein the proximal portion of said guide tip has a larger profile than the distal portion of said guide tip.

4. The filter system of claim 1, wherein the guide tip includes a radiopaque marker band.

5. The filter system of claim 1, wherein the guide tip includes a spring coil.

6. The filter system of claim 5, wherein the spring coil includes a radiopaque material.

7. The filter system of claim 1, wherein the distal portion of said guide tip is atraumatic.

8. The filter system of claim 1, wherein the guidewire lumen of said guide tip is substantially straight.

9. The filter system of claim 1, wherein the guidewire lumen of said guide tip includes a curved portion.

10. The filter system of claim 1, wherein the proximal portion of said guide tip includes a tapered hole, and wherein the distal end of said elongated wire is attached to the guide tip at said tapered hole.

11. The filter system of claim 1, wherein the proximal portion of said guide tip includes a joint, and wherein the distal end of said filter wire is attached to the guide tip at said joint.

12. The filter system of claim 11, wherein the distal end of said elongated wire includes attachment means configured to provide an interference fit with the joint on the proximal portion of said guide tip.

13. The filter system of claim 12, wherein said attachment means is a coil disposed about the distal end of said elongated wire.

14. The filter system of claim 1, wherein the embolic protection filter is adapted to self-deploy when removed from the distal sheath.

15. The filter system of claim 1, wherein the embolic protection filter comprises a filter membrane operatively coupled to a support hoop and suspension arm, the support hoop forming a mouth for filtering embolic debris within a vessel.

16. The filter system of claim 15, further comprising a radiopaque coil disposed about the support hoop.

17. The filter system of claim 1, wherein the embolic protection filter and guide tip are coupled to a frame.

18. The filter system of claim 17, wherein the frame includes a port and an inner lumen configured to slidably receive the guidewire.

19. The filter system of claim 17, wherein the frame includes a coil.

20. The filter system of claim 17, wherein the frame includes a slotted tube.

21. The filter system of claim 20, wherein the slotted tube includes one or more sections having differing flexibility characteristics.

22. The filter system of claim 1, wherein the proximal portion of said guide tip is configured to slide at least in pan within the distal sheath.

23. The filter system of claim 1, wherein the distal sheath includes one or more skived regions.

24. The filter system of claim 23, wherein said one or more skived regions are interposed between one or more collars.

25. The filter system of claim 1, further comprising a loading tool.

26. The filter system of claim 1, wherein the first lumen of said tubular member includes an end for insertion of the elongated wire, and wherein the second lumen of said tubular member includes a port for insertion of the guidewire.

27. The filter system of claim 26, wherein the end and port terminate at the distal end.

28. The filter system of claim 26, wherein the port is located proximal the end.

29. The filter system of claim 1, further comprising alignment means for radially aligning the guidewire lumen of said guide tip with the second lumen of said elongated tubular member.

30. The filter system of claim 29, wherein said alignment means comprises a key disposed within the distal sheath adapted to slide within a corresponding groove formed on the proximal portion of said guide tip.

31. The filter system of claim 1, further comprising a multiple-lumen retrieval sheath.

32. The filter system of claim 31, wherein the multiple-lumen retrieval sheath includes a first lumen adapted to receive the elongated wire, embolic protection filter, and the proximal portion of the guide tip, and a second lumen adapted to receive a second guidewire.

33. The filter system of claim 32, further comprising a longitudinal slit extending along at least a portion of the second lumen.

34. The filter system of claim 31, wherein the multiple-lumen retrieval sheath is configured for single operator exchange in the body.

35. The filter system of claim 1, wherein the guide tip guidewire lumen has a proximal opening that is distal of the distal end of the elongated wire.

36. The filter system of claim 1, wherein the proximal portion of the guide tip has an elongate axis and wherein the distal portion of the guide tip has an elongate axis, wherein the proximal portion elongate axis is parallel to and offset from the distal portion elongate axis.

37. The filter system of claim 36 wherein the guidewire lumen has a proximal end that is distal of the proximal portion of the guide tip.

38. A filter system, comprising:
a guide tip having a proximal portion and a distal portion, the guide tip defining a guidewire lumen therethrough, said lumen having a proximal port and a distal port adapted to receive and slidably pass a guidewire;
an elongated wire having a proximal end and a distal end, the distal end of said elongated wire attached to the proximal portion of said guide tip at a point of attachment;
an embolic protection filter disposed along the elongated wire;
an elongated tubular member extending distally to a distal end, the elongated tubular member defining a first lumen, having a proximal and distal end, adapted to receive the elongated wire, and a second lumen, having a proximal and a distal port, adapted to receive the guidewire; wherein, when the guidewire is present in use, the embolic protection filter is collapsible at least in part within the distal end of the elongated tubular member, further wherein, when the embolic protection filter is collapsed in part within the distal sheath, a portion of the guidewire within the second lumen of the elongated tubular member adjacent the distal port of the second lumen is generally coplanar with a portion of the guidewire within the guidewire lumen of the guide tip, a portion of the elongated wire within the first lumen of the elongated tubular member adjacent the distal end of the first lumen, and the point of attachment of the elongated wire to the guide tip; and
a multiple-lumen retrieval sheath adapted to receive a second guidewire.

* * * * *

UNITED STATES PATENT AND TRADEMARK OFFICE
CERTIFICATE OF CORRECTION

PATENT NO. : 7,651,514 B2
APPLICATION NO. : 10/734849
DATED : January 26, 2010
INVENTOR(S) : Salahieh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1249 days.

Signed and Sealed this

Twenty-third Day of November, 2010

David J. Kappos
*Director of the United States Patent and Trademark Office*